US00PP37773P2

(12) United States Plant Patent
Sisti

(10) Patent No.: US PP37,773 P2
(45) Date of Patent: Oct. 13, 2026

(54) ***ALOCASIA* PLANT NAMED 'SISTILIB'**

(50) Latin Name: ***Alocasia puncakborneensis* x *cuprea***
Varietal Denomination: SISTILIB

(71) Applicant: Lindsay Sisti, Oak Park, IL (US)

(72) Inventor: Lindsay Sisti, Oak Park, IL (US)

( * ) Notice: Subject to any disclaimer, the term of this patent is extended or adjusted under 35 U.S.C. 154(b) by 0 days.

(21) Appl. No.: 19/639,393

(22) Filed: Apr. 6, 2026

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

(56) References Cited

U.S. PATENT DOCUMENTS

PP35,554 P2 * 12/2023 Sisti ..... A01H 6/10
Plt./373

* cited by examiner

*Primary Examiner* — Karen M Redden

(74) *Attorney, Agent, or Firm* — James R. Holm; Plant Novelty Rights, LLC

(57) ABSTRACT

A new and distinct *Alocasia* plant named 'SISTILIB' particularly distinguished by: dark green adaxial leaf coloration with an iridescent sheen; bullate leaves with deeply incised venation on the adaxial surface; broad, ovate shaped leaves; yellow-green colored petioles; and robust growth habit.

6 Drawing Sheets

Figure 1:
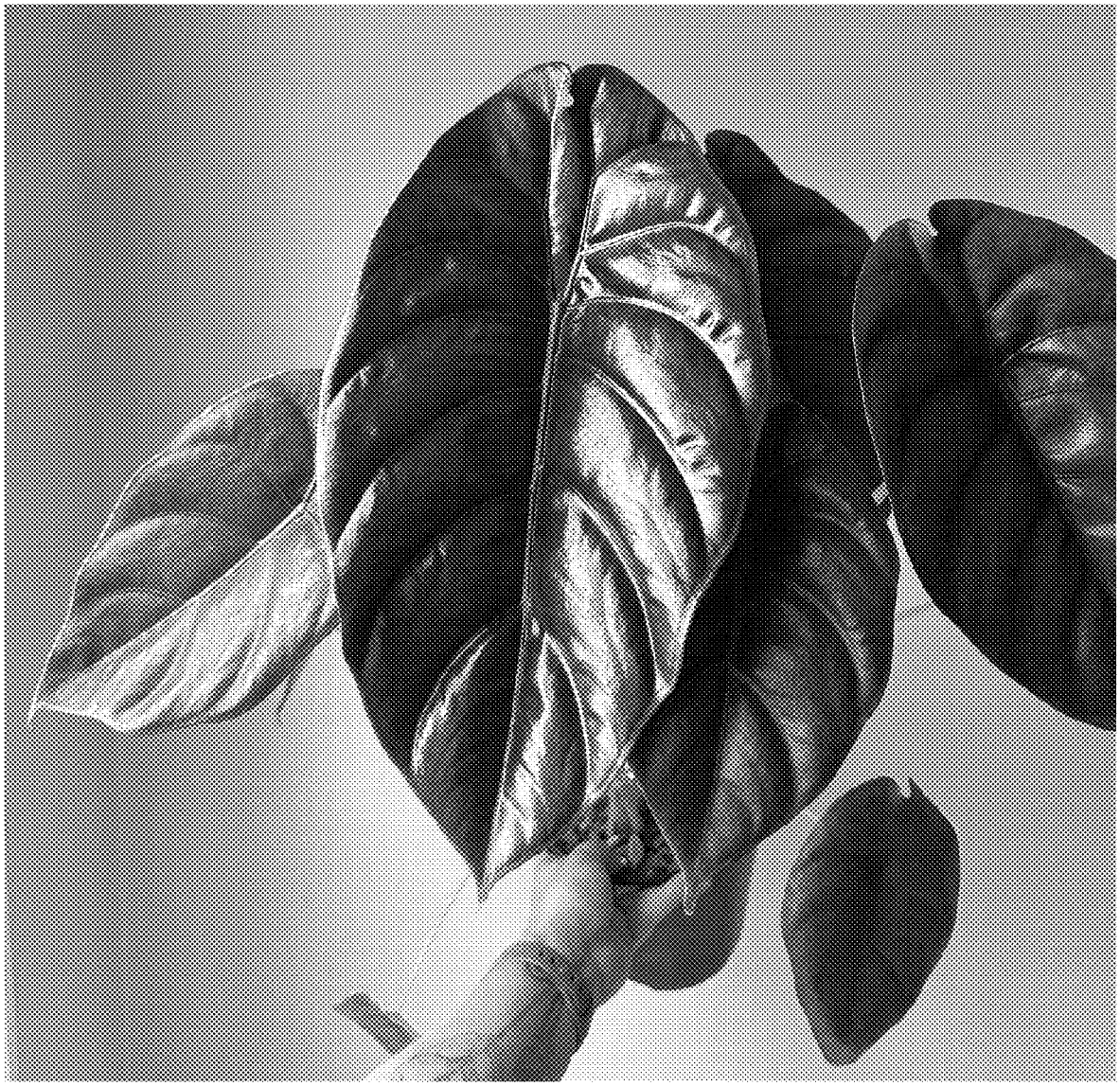

Genus and species: *Alocasia puncakborneensis* x *cuprea*.
Variety denomination: 'SISTILIB'.

BACKGROUND OF THE NEW PLANT

The present invention comprises a new and distinct interspecific hybrid plant of *Alocasia*, hereinafter referred to by its cultivar name 'SISTILIB'.

The new cultivar was derived from a controlled breeding program conducted by the Inventor in Oak Park, Illinois. The overall purpose of the breeding program is to make new selections of *Alocasia* plants that are compact, have unique and colorful foliage and improved hardiness and vigor. 'SISTILIB' is the product of a controlled cross made by the inventor in March 2024 between the species *Alocasia puncakborneensis* (unpatented) as the female parent or seed parent and the species *Alocasia cuprea* (unpatented) as the male parent or pollen parent. Mature berries from said cross were collected in August 2024 and planted in a soilless media. 'SISTILIB' was selected by the inventor in May 2025 as a single unique plant from amongst progeny plants derived from said cross.

The new cultivar was selected based on its attractive, wide ovate leaf blade, the rich green iridescent adaxial leaf surface coloration, its deeply incised leaf venation giving the leaves a shiny, "pillowy" bullate appearance and its robust growth habit. 'SISTILIB' was first reproduced asexually from corms in May 2025 in Oak Park, Illinois. Asexual reproduction by corms has shown that the unique features of the new cultivar are stable and reproduced true-to-type in successive generations.

Plant Breeder's Rights for this variety have not been applied for. 'SISTILIB' has not been made publicly available or sold anywhere in the world prior to the effective filing date of this application.

SUMMARY OF THE INVENTION

The new *Alocasia* cultivar has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *Alocasia* cultivar. The combination of these characteristics distinguishes 'SISTILIB' as a new and distinct cultivar of *Alocasia:*

1. Dark green adaxial leaf coloration with an iridescent sheen;
2. Bullate leaves with deeply incised venation on the adaxial surface;
3. Broad, ovate shaped leaves;
5. Yellow-green colored petioles; and
6. Robust growth habit.

DESCRIPTION OF THE PHOTOGRAPHS

This new *Alocasia* cultivar is illustrated by the accompanying-colored photographs which show the overall appearance and distinct characteristics of the plant. The colors shown are as true as can be reasonably obtained by conventional photographic procedures. The photographs are of one-year-old plants grown in 9-inch containers inside a plant growth room receiving bright, indirect natural light and with average temperatures between 65 and 75 degrees F. and under approximately 35 to 50 percent relative humidity in Oak Park, Illinois. Colors in the photographs may differ slightly from the color values cited in the botanical description which accurately describes the colors of the new variety.

FIG. 1. shows an overhead view of the overall plant form and foliage of 'SISTILIB'.

Figure 2:
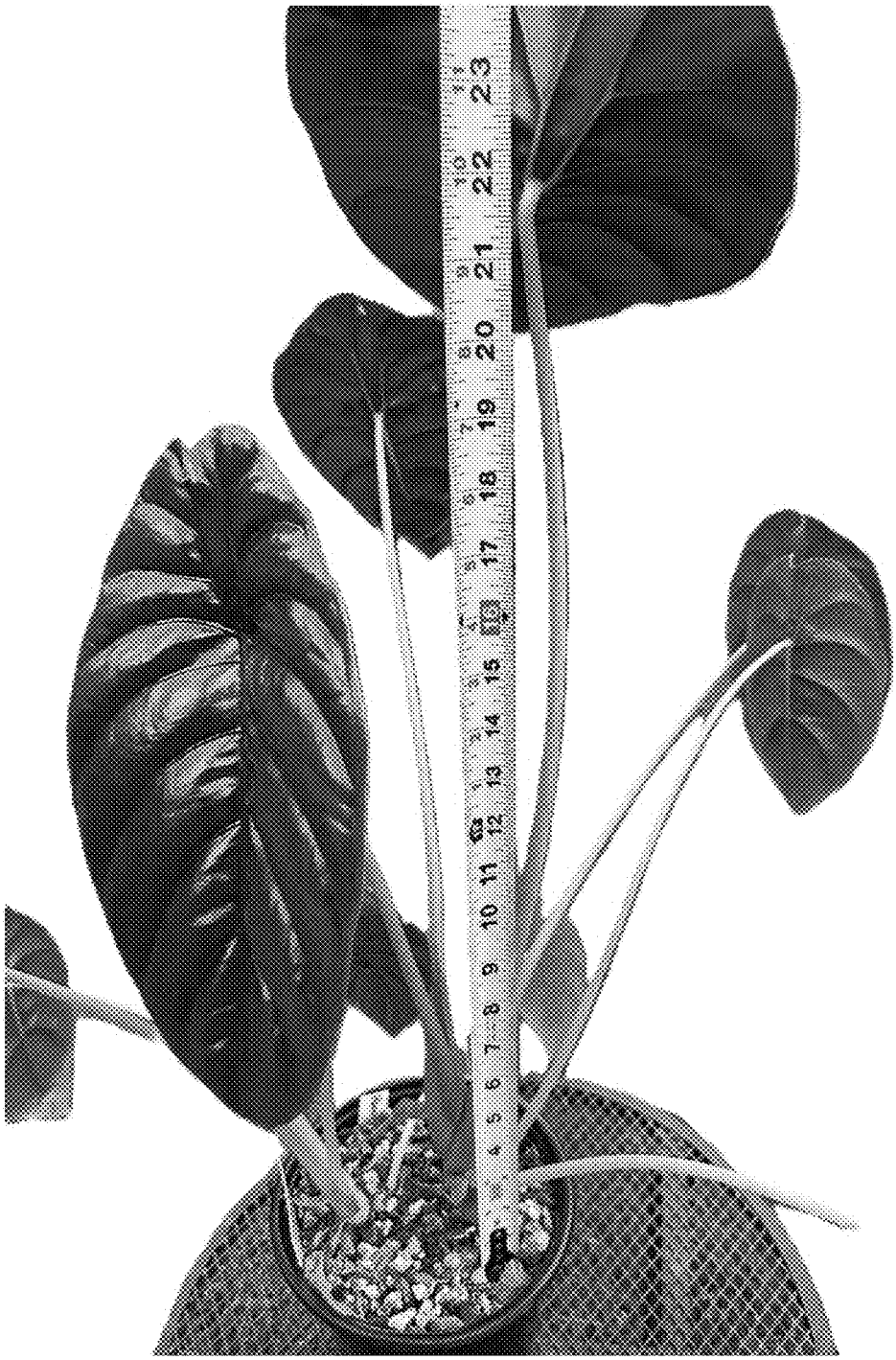

FIG. 2. shows a side view of the overall plant form and foliage of 'SISTILIB' with size reference to a standard measuring tape.

Figure 3:
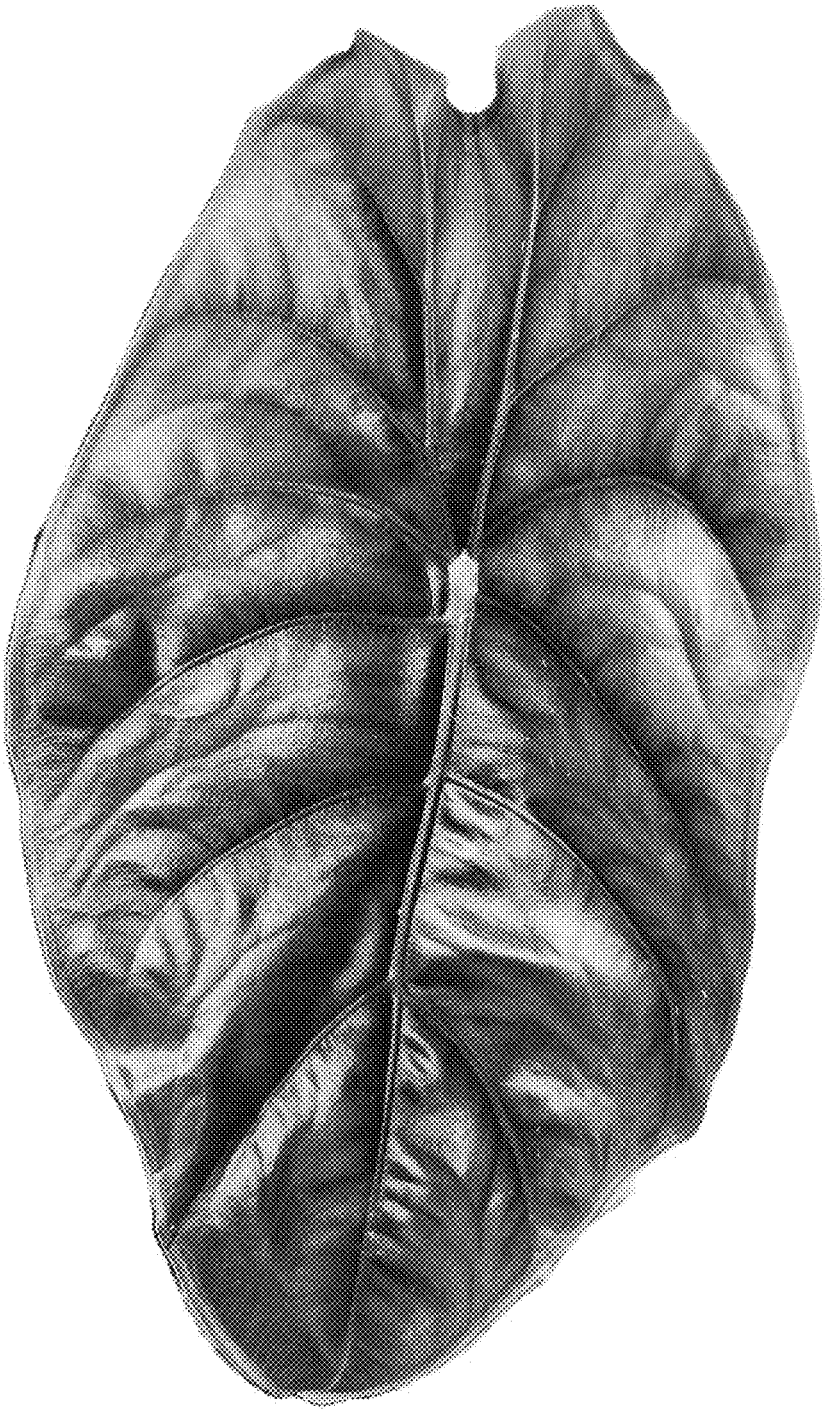

FIG. 3. shows a close-up of the adaxial surface of a typical immature leaf of 'SISTILIB'.

Figure 4:
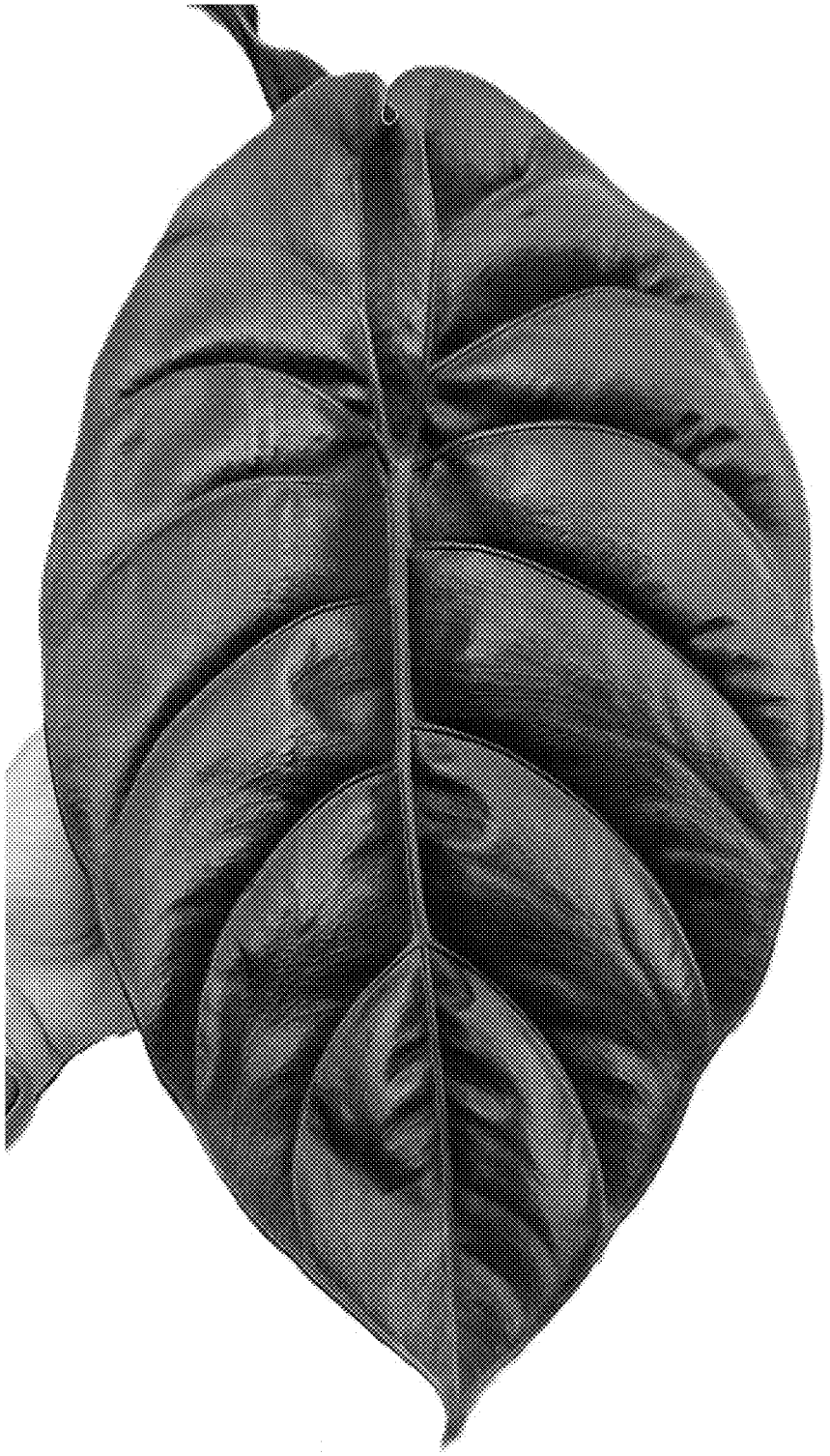

FIG. 4. shows a close-up of the adaxial surface of a typical mature leaf of 'SISTILIB'.

Figure 5:
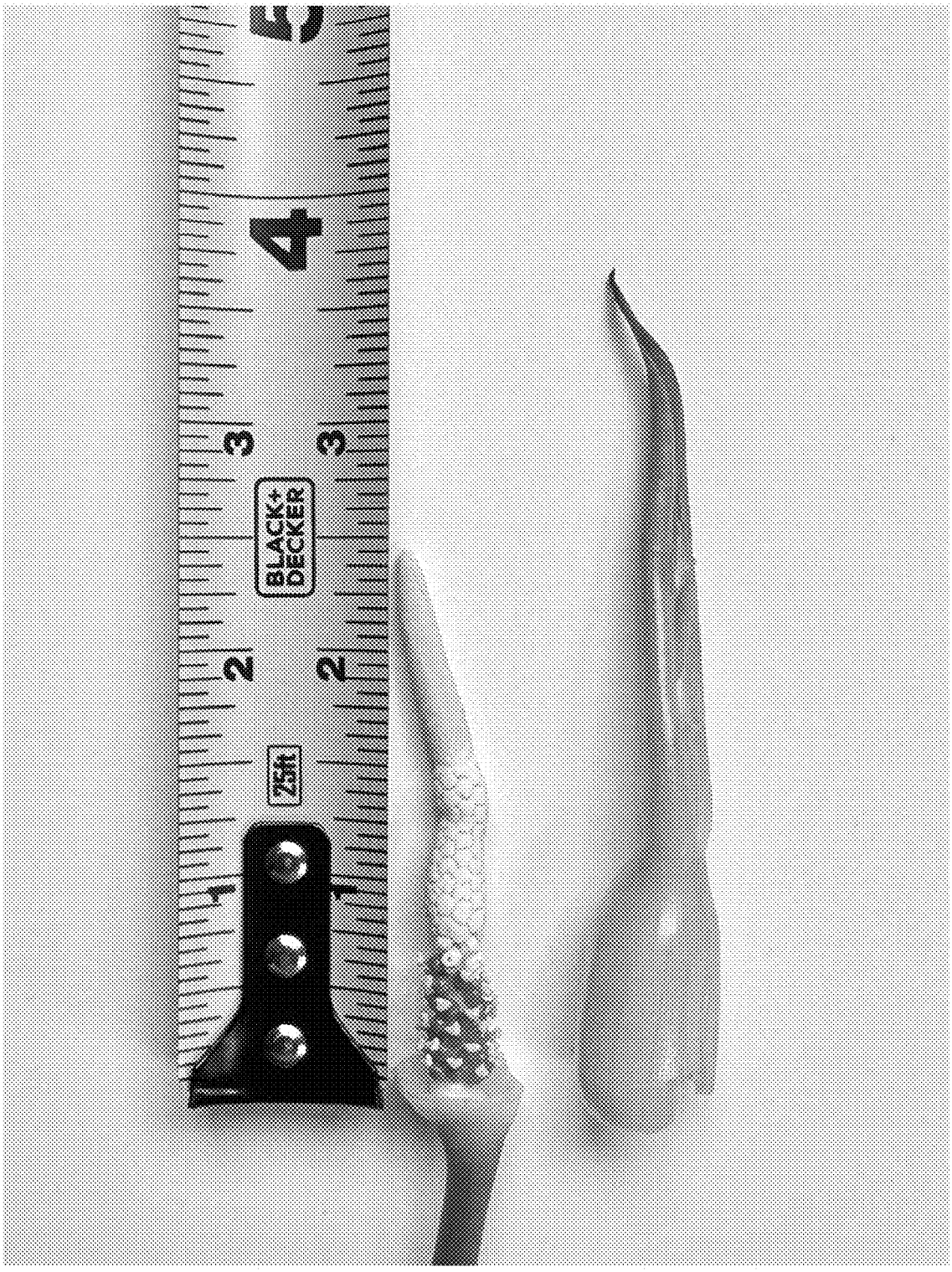

FIG. 5. shows typical inflorescence observed on plants of 'SISTILIB' with the spathe (right) removed to show the inner spadix (center) with size reference to a standard measuring tape (left).

Figure 6:
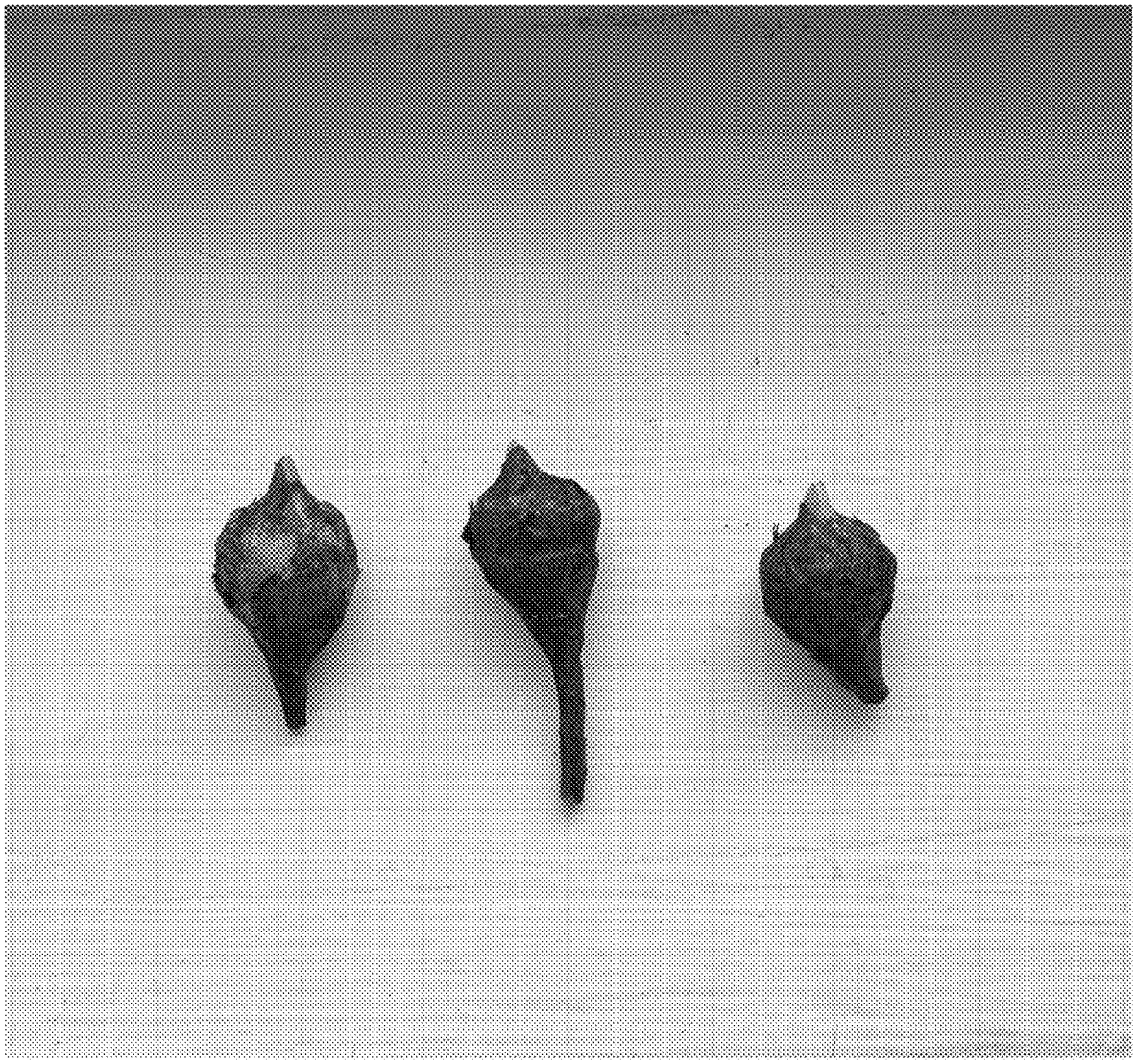

FIG. 6. shows typical corms observed on plants of 'SISTILIB'.

DETAILED BOTANICAL DESCRIPTION OF THE PLANT

The following is a detailed description of one-year-old plants grown in 9-inch containers inside a plant growth room receiving bright, indirect natural light and with average temperatures between 65 and 75 degrees F. and under approximately 35 to 50 percent relative humidity in Oak Park, Illinois. Observations and measurements were taken in October 2025 under natural light in Oak Park, Illinois and in Mount Dora, Florida. Measurements and numerical values represent averages of typical plant types. Color references are made to The Royal Horticultural Society Colour Chart, Sixth Edition, except where general color terms of ordinary dictionary significance are used.

Classification:

*Family.*—Araceae.

*Botanical.*—*Alocasia puncakborneensis* x *cuprea.*

*Common.*—*Alocasia*or Elephant Ear.

*Denomination.*—'SISTILIB'.

General description:

*Plant type.*—Tropical perennial.

*Plant and growth habit.*—Open and upright to outwardly arching.

*Height from soil level to top of foliar plane.*—Approximately 50.0 cm.

*Plant spread.*—Approximately 45.0 cm.

*Primary stem thickness.*—Approximately 3.0 cm when measured at the base above the soil level.

*Growth rate.*—Approximately 50 cm of growth per year.

*Propagation type.*—Corms.

*Roots.*—Thin, fibrous and fleshy; typically white to light brown in color, actual color of the roots dependent on substrate composition, water quality, fertilizer, substrate, temperature and age of roots.

*Corms.*—General: Roughly semi-deltoid in shape and comprised of fibrous scales covering a translucent, fleshy interior. Length: Approximately 1.8 cm. Width: Approximately 1.1 cm. Color: N170D (moderate yellowish pink) underneath fibrous scales; fibrous scales colored 166A (greyish brown).

*Time required to produce a young plant from corms.*—Approximately 4 months.

Foliage description:

*Quantity of leaves.*—7.

*Arrangement.*—Whorled.

*Attachment.*—Petiolate.

*Division.*—Simple.

*Lamina.*—Shape and appearance: Broadly ovate, bullate between the primary vein and secondary veins on the adaxial surface. Aspect: Slightly to moderately concave. Length: Approximately 32.5 cm when measured along the center axis of the foliar plane. Width: Approximately 19.8 cm at the widest point above the leaf base. Orientation: Pendulous. Apex: Caudate, about 2.0 cm in length. Base: Lobate-cordate, lobes are about 3.3 cm in width when measured from the outer leaf margin to the inner apex of the sinus; sinus is narrow and shallow, approximately 1.8 cm in depth with lobe bases occasionally slightly overlapping. Margins: Entire, slightly undulate. Texture and luster (juvenile foliage): Adaxial surface: Coriaceous, glabrous, and slightly glossy. Abaxial surface: Coriaceous, glabrous, and slightly glossy to matte. Texture and luster (mature foliage): Adaxial surface: Coriaceous, glabrous, and glossy. Abaxial surface: Coriaceous, glabrous, and glossy. Venation pattern: Pinnate, one primary vein (midvein) bifurcating at the basal notch and approximately 14 secondary veins with numerous veinlets appearing in a netted pattern. Color: Juvenile foliage, adaxial surface: Interveinal areas: Overall N144A (strong yellowish green) with N189A (dark greyish green) flanking the primary vein and secondary veins. Primary vein: N189A (dark greyish green). Secondary veins: N189A (dark greyish green) with faint 144A (strong yellow green) towards and near the leaf margin. Margin: 144A (strong yellow green). Basal notch: N189A (dark greyish green). Juvenile foliage, abaxial surface: Interveinal areas: N186C (dark greyish red). Primary vein: 144B to 144C (strong yellow green). Secondary veins: Mixture of 144C (strong yellow green) and N186C (dark greyish red) especially towards and near the leaf margin. Veinlets: Faint background coloration of 144C (strong yellow green) with some N186C (dark greyish red) visible as a foreground coloration. Margin: 144B (strong yellow green) along the extreme edge and N186C (dark greyish red) along the inner edge. Mature foliage, adaxial surface: Interveinal areas: A foreground coloration of N189A (dark greyish green) with a slight background coloration of 144A (strong yellow green). Primary vein: N189A (dark greyish green). Secondary veins: N189A (dark greyish green). Margin: 144A (strong yellow green) along the extreme edge and N189A (dark greyish green) along the inner edge. Mature foliage, abaxial surface: Interveinal areas: N77A (greyish purple). Primary vein: 144C (strong yellow green). Secondary veins: 144C (strong yellow green) diffused with N77A (greyish purple). Veinlets: Faint background coloration of 144C (strong yellow green) with some N77A (greyish purple) visible as a foreground coloration. Margin: 144A (strong yellow green) along the extreme edge and mixture of 144A (strong yellow green) and N77A (greyish purple) along the inner edge.

*Petioles.*—Strength: Strong, flexible. Orientation: Outwardly arching and curved downwards through the center to the lamina attachment. Length (mature foliage): Approximately 46.0 to 55.0 cm when measured from the apex of the petiole wing to the point of attachment to the lamina. Diameter (mature foliage): Approximately 1.2 cm above petiole wing and tapering to 0.5 cm at the point of attachment to the lamina. Texture and luster: Smooth, glabrous and shiny. Color: 144A to 144B (strong yellow green) and weakly striated with N77B (greyish purplish red) along the outside surface from the base to near the center. Wings: Length: Approximately 4.3 cm.

Width: Approximately 1.5 to 2.0 cm at the base and then narrowing to an acute apex. Texture and luster (both inner and outer surfaces): Smooth, glabrous and shiny. Color: Inner surface: A translucent 157A (pale yellow green) with N77A to N77B (greyish purplish red) visible within the venation. Edges: N77A (greyish purple) and N186C (dark greyish red). Outer surface: 144A to 144B (strong yellow green) and strongly striated with N77A (greyish purple) and N186C (dark greyish red). Sheath: Shape: Lanceolate and folding around the developing leaf, narrow at the apex. Color: Very weak 144A to 144B (strong yellow green) and heavily striated with N186C (dark greyish red) then becoming brown and desiccated as leaves mature.

Inflorescence:

*Peduncle.*—Length: Approximately 15.3 cm. Diameter: Approximately 1.2 cm. Color: 144A to 144B (strong yellow green).

*Spathe.*—Type: Hooded bract, subtending the spadix. Shape: Lanceolate above female zone, semi-elliptical surrounding female zone. Apex: Aristate. Base: Truncate. Length: 9.5 cm. Width/diameter: Approximately 1.0 cm at the widest point above female zone and tapering to the apex; approximately 1.6 cm surrounding female zone. Color (outer surface): 145C (light yellow green) and then gradually darkening to 144A to 144B (strong yellow green) above female zone to the apex.

*Spadix.*—Length: Approximately 6.0 cm. Appendix zone: Shape: Lanceolate. Apex: Broadly pointed. Length: 2.4 cm. Width: 0.5 cm at the base and narrowing acutely at the apex. Color: 158A (pale yellow). Male zone: Shape: Roughly cylindrical and constricted approximately 0.5 cm below the appendix zone. Length: 1.9 cm. Width: 0.64 cm. Color: NN155A (yellowish white). Sterile zone: Length: 0.32 cm. Width: 0.32 cm. Color: NN155A (yellowish white). Female zone: Shape: Cylindrical. Length: 1.3 cm. Width: 0.8 cm. Color: 144A (strong yellow green).

Cold tolerance: None observed to date.

Disease and pest tolerance: None observed to date.

Fruit and seed set: None observed to date.

Drought tolerance: None observed to date.

COMPARISON WITH PARENTAL VARIETIES

'SISTILIB' differs from the female parent species *Alocasia puncakborneensis* in that 'SISTILIB' has leaves that are broadly ovate, leathery in texture and more deeply bullate between the main vein and secondary veins on the adaxial surface, whereas the female parent has leaves that are much narrower, more elongated, and more bullate, especially between the tertiary venation on the adaxial surface. 'SISTILIB' has juvenile leaves that are glossy on the adaxial leaf surface, whereas the female parent has both juvenile and mature leaves that are matte on the adaxial leaf surface. Additionally, the sinus opening at the base of leaves of 'SISTILIB' is very shallow to almost inconspicuous on mature leaves, whereas the sinus opening at the base of leaves of the female parent is deeper and much more conspicuous on mature leaves.

'SISTILIB' differs from the male parent species *Alocasia cuprea* in that mature leaves of 'SISTILIB' are colored greyish green with a slight background coloration of yellow-green on the adaxial surface, whereas mature leaves of the male parent have a strong foreground coloration of purplish red with greyish green flanking the primary vein and secondary veins. Additionally, plants of 'SISTILIB' have a more open and upright habit with longer petioles, whereas plants of the male parent have a more compact habit with shorter petioles.

COMPARISON WITH COMMERCIALLY KNOWN VARIETIES

When 'SISTILIB' is compared to the commercial *Alocasia* cultivar 'Dragon Scale' (not patented), 'SISTILIB' has leaves that are larger in size, thinner, and greyish green in color with a slight background coloration of yellow-green on the adaxial surface, whereas leaves of 'Dragon Scale' are smaller in size, thicker, and dark green and pale grey in color on the adaxial surface. Leaves of 'SISTILIB' are glabrous on the adaxial surface, whereas leaves of 'Dragon Scale' are coriaceous and matte. Additionally, 'SISTILIB' has longer petioles and a less compact growth habit compared to 'Dragon Scale'.

I claim:

1. A new and distinct variety of *Alocasia* plant named 'SISTILIB', substantially as illustrated and described herein.

* * * * *